United States Patent
Thompson et al.

(10) Patent No.: US 11,565,986 B2
(45) Date of Patent: Jan. 31, 2023

(54) ETHYLENE SEPARATIONS USING SMALL PORE ZEOLITES CONTAINING DOUBLE-SIX RINGS AND CAGES

(71) Applicant: CHEVRON U.S.A. INC., San Ramon, CA (US)

(72) Inventors: Joshua A. Thompson, Martinez, CA (US); Dan Xie, El Cerrito, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 17/388,105

(22) Filed: Jul. 29, 2021

(65) Prior Publication Data

US 2022/0064087 A1  Mar. 3, 2022

Related U.S. Application Data

(60) Provisional application No. 63/072,458, filed on Aug. 31, 2020.

(51) Int. Cl.
| C07C 7/13 | (2006.01) |
| B01D 53/047 | (2006.01) |
| B01J 20/16 | (2006.01) |
| C07C 7/00 | (2006.01) |

(52) U.S. Cl.
CPC .............. *C07C 7/13* (2013.01); *B01D 53/047* (2013.01); *B01J 20/165* (2013.01); *C07C 7/005* (2013.01); *B01D 2253/1085* (2013.01); *B01D 2256/24* (2013.01); *B01D 2257/102* (2013.01); *B01D 2257/108* (2013.01); *B01D 2257/7022* (2013.01); *B01D 2259/402* (2013.01); *B01D 2259/40013* (2013.01); *B01D 2259/40035* (2013.01); *B01J 2220/56* (2013.01)

(58) Field of Classification Search
None
See application file for complete search history.

(56) References Cited

U.S. PATENT DOCUMENTS

| 2018/0257019 A1* | 9/2018 | Thompson | .............. C10L 3/102 |
| 2022/0062812 A1* | 3/2022 | Thompson | .............. B01D 53/02 |
| 2022/0143544 A1* | 5/2022 | Thompson | .............. B01J 20/18 |

* cited by examiner

*Primary Examiner* — Tam M Nguyen
(74) *Attorney, Agent, or Firm* — Howard Owens (57) ABSTRACT

The present invention describes a process to separate ethylene products from impurities such as nitrogen, hydrogen, ethane, propane and isobutane without the need for distillation processes.

9 Claims, 6 Drawing Sheets

Gas adsorption isotherms of C2H4, C2H6, CH4, N2, and C3H8 on H-SSZ-98-A at 30 degrees C.

Figure 1: Gas adsorption isotherms of C2H4, C2H6, CH4, N2, and C3H8 on H-SSZ-98-A at 30 degrees C.

Figure 2: Gas adsorption isotherms of C2H4, C2H6, CH4, N2, and C3H8 on H-SSZ-98-B at 30 degrees C.

Figure 3: Gas adsorption isotherms of C2H4, C2H6, CH4, N2, and C3H8 on SSZ-105-A at 30 degrees C.

Figure 4: Gas adsorption isotherms of C2H4, C2H6, CH4, N2, and C3H8 on SSZ-105-B at 30 degrees C.

Figure 5: Gas adsorption isotherms of C2H4, C2H6, CH4, N2, and C3H8 on SSZ-105-C at 30 degrees C.

Figure 6: Kinetic uptake of C2H4 on SSZ-98 samples at 30 degrees C.

Figure 7: Kinetic uptake of C2H6 on SSZ-98 samples at 30 degrees C.

Figure 8: Kinetic uptake of C3H8 on SSZ-98 samples at 30 degrees C.

Figure 9: Kinetic uptake of C2H4 on SSZ-105 samples at 30 degrees C.

Figure 10: Kinetic uptake of C2H6 on SSZ-105 samples at 30 degrees C.

Figure 11: Kinetic uptake of C3H8 on SSZ-105 samples at 30 degrees C.

ETHYLENE SEPARATIONS USING SMALL PORE ZEOLITES CONTAINING DOUBLE-SIX RINGS AND CAGES

FIELD

The present invention relates to separation of ethylene products from impurities such as nitrogen, hydrogen, ethane, propane and isobutane without the need for distillation processes.

BACKGROUND

Ethylene-ethane separations for current commercial applications require the use of very large distillation towers and energy requirements in order to separate ethylene to a polymer-grade level. In the polyethylene plant there are stranded gas streams containing significant ethylene content, ranging from 50 to greater than 90 mol %. Due to the intensive process currently used, these gas streams cannot be recycled or recovered at smaller scales. In prior art, some membrane technologies have been developed that have moderate ethylene membrane selectivity, typically less than 10.

Pressure-swing adsorption (PSA) technology is an alternative technology for recovering stranded ethylene in a polyethylene plant that uses a solid adsorbent material to remove impurities that include ethane, hydrogen, nitrogen and methane gas. The adsorbent selection can function as either an equilibrium-based or kinetic-based separation. In principle, all adsorption processes utilize at least two steps: adsorption or uptake of the target molecule in the adsorbent; and desorption or removal of the same target molecule from the adsorbent. This may be achieved by changes in concentration, pressure, or temperature. In the case of PSA and vacuum-swing adsorption (VSA), pressure changes are used to regenerate the adsorbent. PSA does not require a dehydration step necessarily prior to separation of target components. PSA technology is able to treat stranded ethylene gas to recover ethylene up to a target purity of at least 98 mol % without the use of distillation or other thermally-driven separation processes.

It would be desirable to have a PSA or VSA process utilizing an adsorbent material which would require lower vacuum power consumption or elimination of vacuum entirely while allowing for improved recovery of ethylene product. Such a process would enable deployment and competitive use of PSA units to recover stranded ethylene gases.

SUMMARY

In one embodiment, a method is provided for removing impurities found in a polyethylene plant from a stranded ethylene gas stream. These impurities include methane, nitrogen, hydrogen and ethane, but may also include propane and isobutane.

Another embodiment of the method includes alternating input of the feed gas stream between at least two beds of adsorbent particles comprising a zeolite SSZ-98 or SSZ-105 such that the feed gas stream contacts one of the at least two beds at a given time in an adsorption step and a tail gas stream is simultaneously vented from another of the at least two beds in a desorption step. The contact occurs at a feed pressure of from about 50 to about 500 psia for a sufficient period of time to preferentially adsorb ethylene over other impurities in the gas stream. A product gas stream is produced containing no greater than 2 mol % of impurities and at least 98 mol % purity of ethylene. The feed gas stream is input at a feed end of each bed. The product gas stream is removed by depressurization of the bed and desorption of ethylene adsorbed on the zeolite adsorbent SSZ-98 or SSZ-105. The impurity stream is produced in less than the feed composition of ethylene and utilized as a fuel gas or other gas stream within the polyethylene plant.

DETAILED DESCRIPTION

The methods of the present disclosure use SSZ-98 and/or SSZ-105 zeolite particles as an adsorbent material in a cyclic adsorption process for upgrading ethylene product from at least 50 mol % to at least 98 mol %. The other components in the stream can be ethane and larger hydrocarbons as well as N2, CH4 and H2.

In one embodiment, methods and processes of the present disclosure use alternative adsorbent particles that comprise a zeolite SSZ-98 or a zeolite SSZ-105 to remove the contaminants from a feed gas stream. Zeolites are crystalline solids structures made of silicon, aluminum and oxygen that form a framework with cavities and channels inside where cations, water and/or small molecules may reside. Zeolites are crystalline aluminosilicates with open 3D framework structures built of SiO4 and AlO4 tetrahedra linked to each other by sharing all the oxygen atoms to form regular intra-crystalline cavities and channels of molecular dimensions. A defining feature of zeolites is that their frameworks are made up of 4-coordinated atoms forming tetrahedra. These tetrahedra are linked together by their corners and make a rich variety of beautiful structures. The framework structure may contain linked cages, cavities or channels, which are big enough to allow small molecules to enter. The system of large voids explains the consistent low specific density of these compounds. The aluminosilicate framework is negatively charged and can attract positive cations that reside in the cages as a framework ion and can compensate for the negative charge of the framework.

In one embodiment, the process for removing an impurities from a feed gas stream that is ethylene-rich comprises adjusting a selectivity of an adsorbent for retaining ethylene in a product gas stream by changing the substitution of an ERI phase with a LEV phase in a molecular sieve, or zeolite, having an intergrowth of the ERI phase and the LEV phase.

Zeolite SSZ-98 is an example of a synthetic zeolite with an ERI framework type. Molecular sieves are classified by the Structure Commission of the International Zeolite Association (IZA) according to the rules of the IUPAC Commission on Zeolite Nomenclature. According to this classification, framework type zeolites and other crystalline microporous molecular sieves, for which a structure has been established, are assigned a three letter code and are described in the "Atlas of Zeolite Framework Types," Sixth Revised Edition, Elsevier (2007).

ERI framework type molecular sieves, or zeolites, are characterized by three-dimensional 8-membered-ring pore/channel systems containing double-six-rings (d6R) and cages. Zeolite SSZ-98 is a small pore zeolite containing d6R building units and cages.

U.S. Pat. Nos. 9,409,786 and 9,416,017 disclose an ERI framework type molecular sieve designated zeolite SSZ-98 and its synthesis using N,N'-dimethyl-1,4-diazabicyclo[2.2.2]octane dications as a structure directing agent. Zeolite SSZ-98 can also be synthesized using a structure directing agent selected from trimethylphenylammoniun cations, cationic 1,4-diazobicyclo[2.2.2]octane, and combinations thereof. Alternative synthesis methods to make zeolite SSZ-98 are described in U.S. Patent Application Publication No. 2016/0375428.

Zeolite SSZ-105 is an example of a synthetic molecular sieve, or zeolite, that comprises at least one intergrown phase of an ERI framework type molecular sieve and a LEV framework type molecular sieve. Zeolite SSZ-105 can also be described as a molecular sieve having an intergrowth of an ERI phase and a LEV phase. LEV framework-type molecular sieves are also characterized by three-dimensional 8-membered-ring pore/channel systems containing double-six-rings (d6R) and cages. Zeolite SSZ-105 has disordered planar intergrowths of end-member structures ERI and LEV. Zeolite SSZ-105 comprises regions of the ERI framework type sequences and regions of the LEV framework type sequences. Each change from an ERI to an LEV framework type sequence in the zeolite SSZ-105 results in a stacking fault. Any structure directing agent that can make the zeolite SSZ-105 can be used. For example, US20170106357A1 discloses methods to prepare, and compositions of, zeolite SSZ-105 using an N,N-dimethylpiperidinium cation as the structure directing agent.

In one embodiment, the zeolite SSZ-98, the zeolite SSZ-105, or the molecular sieve having an intergrowth of an ERI phase and a LEV phase, has a Si:Al mole ratio of 5 or greater, such as from 5 to 100. In one embodiment, the Si:Al mole ratio can be from greater than 5 to 80, such as from 10 to 50, or from 10 to 35. The Si:Al mole ratio is determined by inductively coupled plasma (ICP) elemental analysis.

In one embodiment the zeolite SSZ-98, the zeolite SSZ-105, or the molecular sieve having an intergrowth of an ERI phase and a LEV phase, is formed into the adsorbent particles by pressing into pellets. In one embodiment, the adsorbent particles can be a component in a membrane that is used for removing the impurities from the feed gas stream that is ethylene-rich. Some examples of mixed-matrix membranes with dispersed adsorbent particles are described in U.S. Pat. No. 6,508,860.

In one embodiment, the zeolite SSZ-98, the zeolite SSZ-105, or the molecular sieve having an intergrowth of an ERI phase and a LEV phase, can be formulated into the adsorbent particles using a combination with other materials, such as binders and/or matrix materials, which provide additional hardness or adsorbent activity to the adsorbent particles. When used, the relative proportions of the zeolite SSZ-98, the zeolite SSZ-105, or the molecular sieve having an intergrowth of an ERI phase and LEV phase, and other materials may vary widely with the zeolite or molecular sieve content ranging from 1 to 90 wt %, or from 2 to 80 wt % of the adsorbent particles.

In one embodiment, the processes can use a molecular sieve having a higher amount of the LEV phase in the intergrowth of the ERI phase and the LEV phase to achieve a particular composition of the product gas. For example, in one embodiment of the process for removing the impurities from the ethylene-rich feed gas stream, the process can comprise: contacting the feed gas stream with adsorbent particles comprising the molecular sieve having an intergrowth of the ERI phase and the LEV phase to provide the product gas stream with less than 2 mol % impurities such as nitrogen, hydrogen, and ethane, and 98 mol % or more ethylene recovered from the feed gas; wherein the LEV phase is from 31 to 99% in the molecular sieve. One example of this type of molecular sieve is zeolite SSZ-105-A, and other zeolite SSZ-105 samples that are described in US 20170106357A1.

In one embodiment, the adsorbent particles are made from a homogeneous mixture and are not coated particles or made from layers of different materials. An example of how these adsorbent particles can be made is when the adsorbent particles are pressed into pellets from a powder. In one embodiment, the zeolite is mixed with a catalyst support and the zeolite and the catalyst support are ground together into a powder that is a homogeneous mixture. In one embodiment the catalyst support is alumina, such as a pseudo-Boehmite alumina powder. The catalyst support can be inert or can participate in the adsorption performed by the adsorbent particles. Typical catalyst supports include various kinds of carbon, alumina, and silica. In one embodiment, the catalyst support comprises an amorphous silica aluminate. In one embodiment, the catalyst support comprises an amorphous silica aluminate and a second support material.

Examples of the catalyst support or the second support material (when used), can include kieselguhr, alumina, silica, and silica-alumina. Other examples include alumina-boria, silica-alumina-magnesia, silica-alumina-titania and materials obtained by adding other zeolites and other complex oxides thereto. In one embodiment, the catalyst support is porous, and comprises a natural clay or a synthetic oxide. The catalyst support can be selected to provide adequate mechanical strength and chemical stability at the contacting conditions under which the adsorbent particles are employed.

In one embodiment, the catalyst support or the second support material comprises a pseudo-boehmite alumina. Examples of pseudo-boehmite alumina are CATAPAL® high purity aluminas. CATAPAL® is a registered trademark of Sasol Limited. The pressed pellets can be broken and sieved to obtain the desired mesh size. In one embodiment, the powder X-ray diffraction (XRD) pattern of the pressed pellets is the same as the original XRD pattern of the zeolite powder prior to it having been pressed into a pellet.

In one embodiment, the zeolite SSZ-98 or the SSZ-105 has a cation as a framework ion. In one embodiment, the molecular sieve having an intergrowth of an ERI phase and a LEV phase has a cation as a framework ion. The cation can be selected from the group consisting of a sodium, a calcium, a potassium, a lithium, a magnesium, a barium, a copper, a silver, a platinum, a paladium, a hydrogen and combinations thereof. In one embodiment, the cation is sodium. In one embodiment, the cation is hydrogen. The choice of the cation can change the adsorption performance of the adsorbent particles.

In one embodiment, the method comprises alternating an input of the feed gas stream between at least two beds of the one or more adsorbent particles. In one embodiment, the at least two beds of the one or more adsorbent particles are up to ten beds of the one or more adsorbent particles. The feed gas stream can contact one of the at least two beds at a given time by an adsorption step and a product gas stream can be simultaneously vented from another of the at least two beds by a desorption step to recover high purity ethylene.

In one embodiment, the desorbed high purity ethylene product stream is compressed to from about 500 to 700 psia and recycled to a polyethylene reactor.

Figure 1:
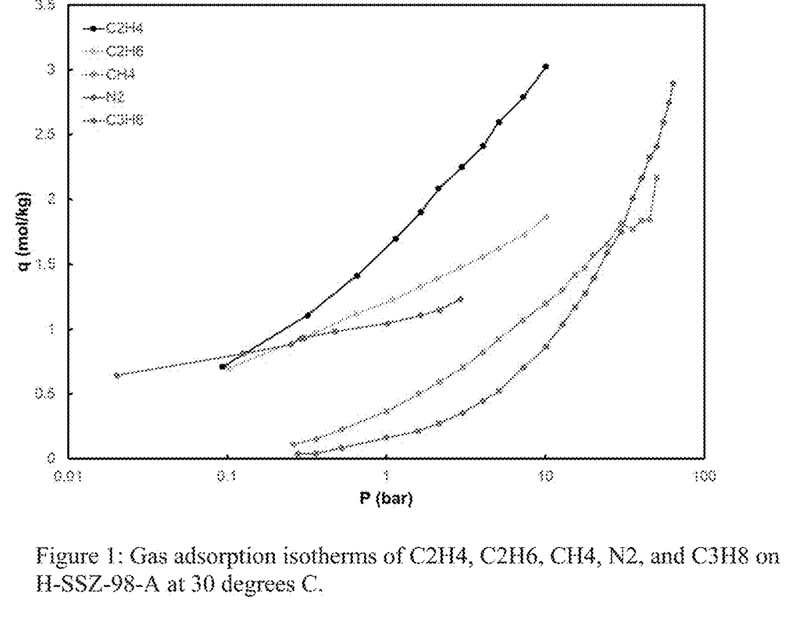
FIG. 1 is a plot of gas adsorption isotherms of C2H4, C2H6, CH4, N2, and C3H8 on H-SSZ-98-A at 30 degrees C.
Figure 2:
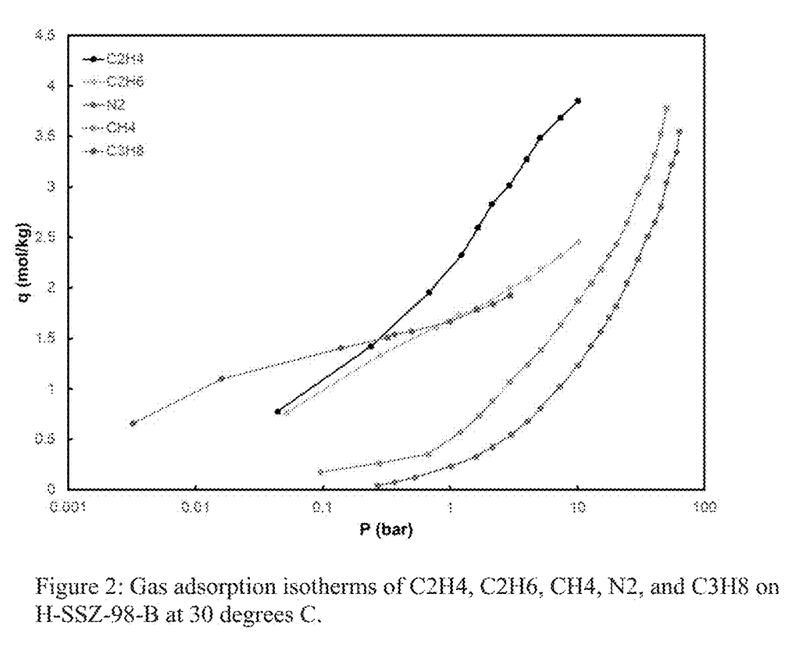
FIG. 2 is a plot of gas adsorption isotherms of C2H4, C2H6, CH4, N2, and C3H8 on H-SSZ-98-B at 30 degrees C.

Referring to FIG. 1, here is shown an exemplary two bed PSA system (100) with two beds. In this figure, a feed gas stream (101) is introduced into line (106) having block valves (105) therein. Line (106) connects the first inlet end (108A) to the first adsorption column (108), and also connects the second inlet end (109A) to the second adsorption column (109). A second line (107), is fluidly connected to line (106) and separately connects the first inlet end (108A) to the first adsorption column (108), and also connects the second inlet end (109A) to the second adsorption column (109). Second line (107) has an outlet for tail gas (110). The first adsorption column (108) contains the adsorbent particles described herein, and has a first product end (108B). The second adsorption column (109) also contains the adsorbent particles described herein, and has a second product end (109B). The first product end (108B) and the second product end (109B) are connected by a third line (111) and by a fourth line (112). The third line (111) and the fourth line (112) contain block valves (105). The fourth line (112) is connected with a fifth line (113), which delivers an intermediate product gas stream to a product gas buffer tank (114). The product gas buffer tank (114) allows for controlled purging and re-pressurization steps. The product gas stream (115) can be provided from the product gas buffer tank (114). The product gas buffer tank is controlled by one or more block valves (105) through a sixth line (116) that connects to the third line (111), as shown.

In one embodiment, wherein the method utilizes two beds of the one or more adsorbent particles, the method further comprises:
(a) following the adsorption step in one of the two beds and a simultaneous desorption step in the other of the two beds, equalizing a pressure of the two beds through the product end of each of the two beds at the end of the adsorption and the simultaneous desorption step; and\
(b) re-pressurizing the bed having just completed the simultaneous desorption step by sending a slipstream of the product gas stream through the product end of the bed having just completed the simultaneous desorption step.

EXAMPLES

Example 1: Synthesis of SSZ-98-A Samples 4.02 g of a 45% KOH solution, 4.75 g of deionized water and 5.00 g of CBV720 Y-zeolite (Zeolyst International, SiO2/Al2O3 mole ratio=60) were mixed together in a TEF-LON® liner. Then, 18.51 g of a 20% trimethylphenylammonium hydroxide solution was added to the mixture. The resulting gel was stirred until it became homogeneous. The liner was capped and placed within a Parr steel autoclave reactor. The autoclave was placed in an oven and heated at 135° C. for 4 days. The solid products were recovered from the cooled reactor by centrifugation, washed with deionized water and dried at 95° C. The resulting zeolite product was identified by powder XRD and SEM as pure SSZ-98.

Example 2: Synthesis of SSZ-98-B Samples 1.56 g of a 45% KOH solution, 7.46 g of deionized water and 2.00 g of CBV720 Y-zeolite (Zeolyst International, SiO2/Al2O3 mole ratio=30) were mixed together in a TEF-LON® liner. Then, 7.17 g of a 20% trimethylphenylammonium hydroxide solution was added to the mixture. The resulting gel was stirred until it became homogeneous. The liner was capped and placed within a Parr steel autoclave reactor. The autoclave was placed in an oven and heated at 135° C. for 4 days. The solid products were recovered from the cooled reactor by centrifugation, washed with deionized water and dried at 95° C.
The resulting zeolite product was identified by powder XRD and SEM as pure SSZ-98.

Example 3: Synthesis of SSZ-105-A Samples 1.20 g 45% KOH solution, 0.19 g 50% NaOH solution and 3.00g CBV780 Y-zeolite powder (Zeolyst International, SiO2/Al2O3 mole ratio=80) were mixed together in a Teflon liner. Then 27.61 g 9.19% N,N-dimethylpiperidinium hydroxide solution was added to the mixture. The resulting gel was stirred until it became homogeneous. The liner was then capped and placed within a Parr Steel autoclave reactor. The autoclave was then put in an oven heated at 150 degree C. for 4 days. The solid products were recovered from the cooled reactor by centrifugation, washed with deionized water and dried at 95 degree C. The resulting zeolite product was identified by powder XRD and SEM as a pure SSZ-105 zeolite. The product had a SiO2/Al2O3 mole ratio of 16.7, as determined by ICP elemental analysis. A comparison between the experimental powder XRD pattern collected from the calcined product and DIFFaX simulated powder XRD patterns with various ERI/LEV intergrowth ratios indicates that the product is an intergrowth material with approximately 50-60% of ERI stacking sequence and 40-50% LEV stacking sequence.

Example 4: Synthesis of SSZ-105-B Samples

The same synthesis procedure as Example 1 was followed except that CBV780 Y-zeolite powder was replaced by CBV720 Y-zeolite powder (Zeolyst International, SiO2/Al2O3 mole ratio=20). The resulting zeolite product was identified by powder XRD and SEM as a pure SSZ-105 zeolite. The product had a SiO2/Al2O3 mole ratio of 13.6, as determined by ICP elemental analysis. A comparison between the experimental powder XRD pattern collected from the calcined product and DIFFaX simulated powder XRD patterns with various ERI/LEV intergrowth ratios indicates that the product is an intergrowth material with approximately 80-90% of ERI stacking sequence and 10-20% LEV stacking sequence.

Example 5: Synthesis of SSZ-105-C Samples 1.51 g 45% KOH solution, 0.39 g 50% NaOH solution and 3.00 g CBV760 Y-zeolite powder (Zeolyst International, SiO2/Al2O3 mole ratio=60) were mixed together in a Teflon liner. Then 27.61 g 9.19% N,N-dimethylpiperidinium hydroxide solution was added to the mixture. The resulting gel was stirred until it became homogeneous. The liner was then capped and placed within a Parr Steel autoclave reactor. The autoclave was then put in an oven heated at 150 degree C. for 4 days. The solid products were recovered from the cooled reactor by centrifugation, washed with deionized water and dried at 95 degree C. The resulting zeolite product was identified by powder XRD and SEM as a pure SSZ-105 zeolite. The product had a SiO2/Al2O3 mole ratio of 14.5, as determined by ICP elemental analysis. A comparison between the experimental powder XRD pattern collected from the calcined product and DIFFaX simulated powder XRD patterns with various ERI/LEV intergrowth ratios indicates that the product is an intergrowth material with approximately 70-80% of ERI stacking sequence and 20-30% LEV stacking sequence.

Example 4: Micropore Characterization

SSZ-98 and SSZ-105 samples were analyzed for micropore volume by N2 physisorption at −196 degree C. Activation at 300 degree C. was performed prior to adsorption to remove residual water adsorbed on the zeolite. A summary in Table 1 shows that the increasing substitution of the ERI phase with the LEV phase reduces the micropore volume slightly while the lower substitution has similar micropore volumes as SSZ-98-B. This intergrowth of LEV-ERI phases with lower pore volume will affect the gas adsorption properties for separation of ethylene from other impurities in gas mixtures as discussed in later examples.

TABLE 1

Summary of SSZ-105 samples

| Zeolite SSZ-105 Sample | ERI Phase (%) | SAR | MPV (cm$^3$/g) |
|---|---|---|---|
| SSZ-98-A | 100 | 19.7 | 0.15 |
| SSZ-98-B | 100 | 15.4 | 0.22 |
| SSZ-105-A | 50-60 | 16.7 | 0.20 |
| SSZ-105-B | 80-90 | 13.6 | 0.22 |
| SSZ-105-C | 80-70 | 14.5 | 0.22 |

Example 5: Pure Component Equilibrium Adsorption

Equilibrium gas adsorption experiments for C2H4, C2H6, CH4, N2, and C3H8 were performed on a HPVA 200-4 port volumetric system. Samples were first activated at 300° C. to obtain the dry weight and then reactivated in the gas adsorption system. Gases used were C2H4, C2H6, CH4, N2, C3H8 and He (all 99.999%). The zeolites were tested from 0-10 bar for both C2H4 and C2H6, 0-65 bar for CH4, 0-65 bar for N2, and 0-3 bar for C3H8.

FIGS. 1-5 show the equilibrium adsorption results for gas adsorption tests. These represent either majority components or majority impurities found in stranded ethylene gas streams in polyethylene plants. If an adsorbent is capable of separating C2H4 from C2H6, CH4, N2 and C3H8, majority ethylene may be recovered, especially in application of gas mixtures with about 50 mol % ethylene in the feed gas. Because the samples have a lower amount of aluminum in the zeolite framework, the ethylene adsorption isotherms do not show saturation at moderate temperatures until the ethylene pressure reaches 10 bar. The ethane adsorption isotherms show lower saturation capacities compared to ethylene, resulting in improved ethylene adsorption selectivity over ethane. In addition, C3H8 shows very similar adsorption behavior as C2H6.

Figure 3:
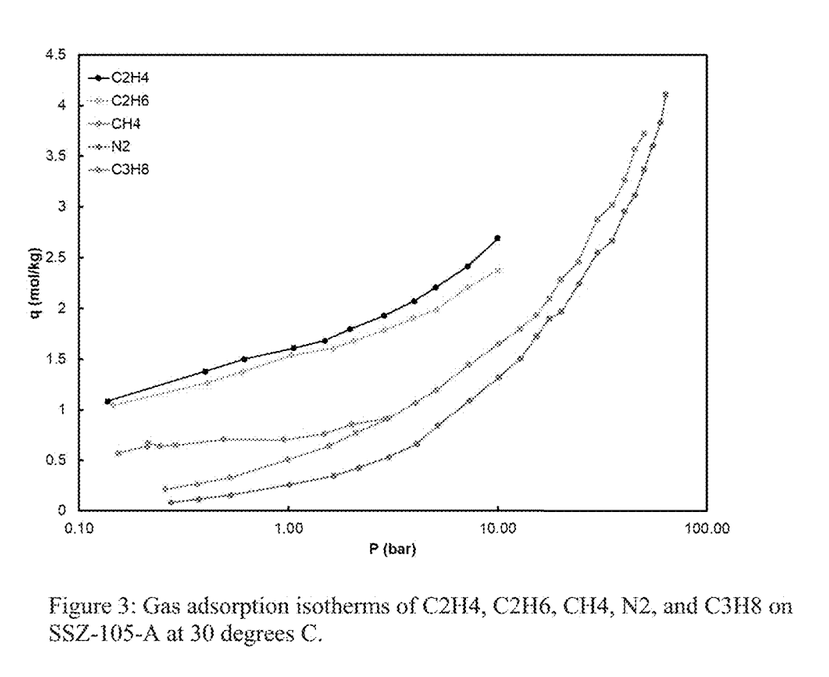
FIG. 3 is a plot of gas adsorption isotherms of C2H4, C2H6, CH4, N2, and C3H8 on SSZ-105-A at 30 degrees C.
Figure 4:
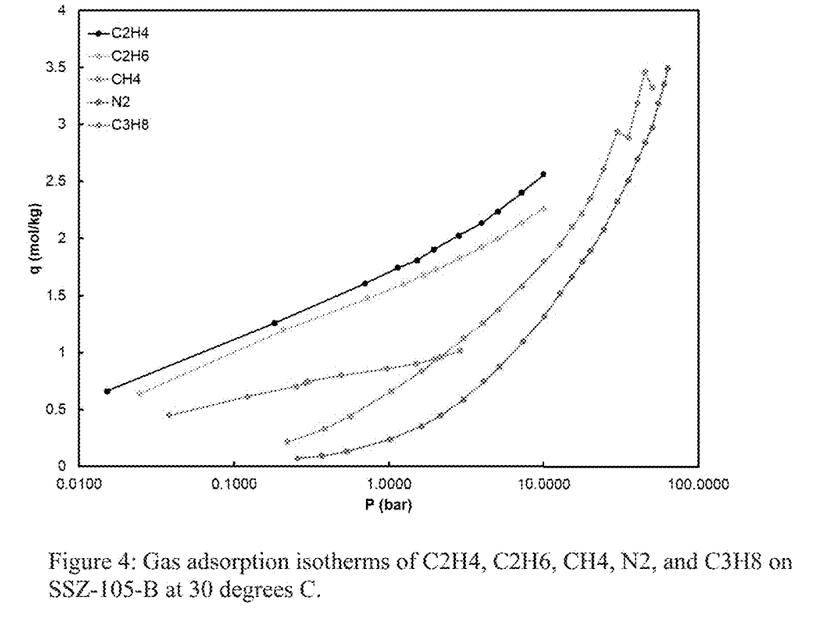
FIG. 4 is a plot of gas adsorption isotherms of C2H4, C2H6, CH4, N2, and C3H8 on SSZ-105-B at 30 degrees C.
Figure 5:
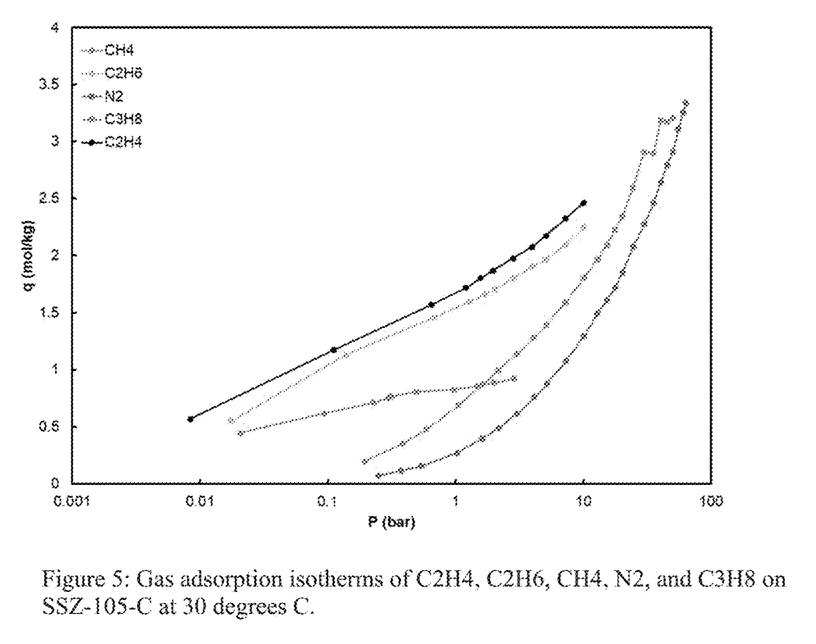
FIG. 5 is a plot of gas adsorption isotherms of C2H4, C2H6, CH4, N2, and C3H8 on SSZ-105-C at 30 degrees C.

Compared to pure SSZ-98 phase zeolites, SSZ-105 has a tunable LEV intergrowth phase that affects the adsorption capacity and affinity for specific gases as shown in FIGS. 3-5. In particular, the adsorption of propane has less capacity when the LEV intergrowth phase is present while the ethylene adsorption capacity is comparable to the pure SSZ-98 phase.

Example 6: Kinetic Uptake of SSZ-98 Adsorbents

Figure 6:
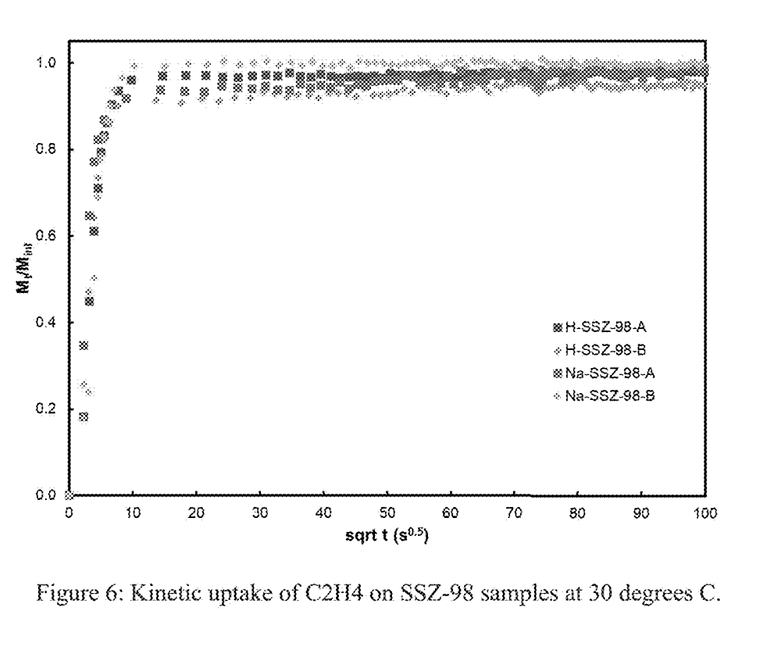
FIG. 6 is a plot of kinetic uptake of C2H4 on SSZ-98 samples at 30 degrees C.
Figure 7:
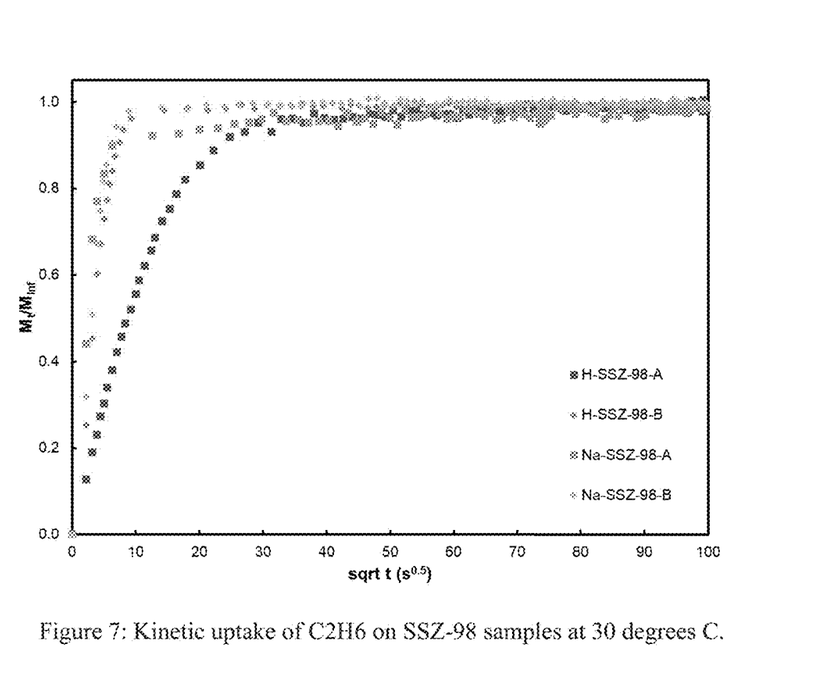
FIG. 7 is a plot of kinetic uptake of C2H6 on SSZ-98 samples at 30 degrees C.
Figure 8:
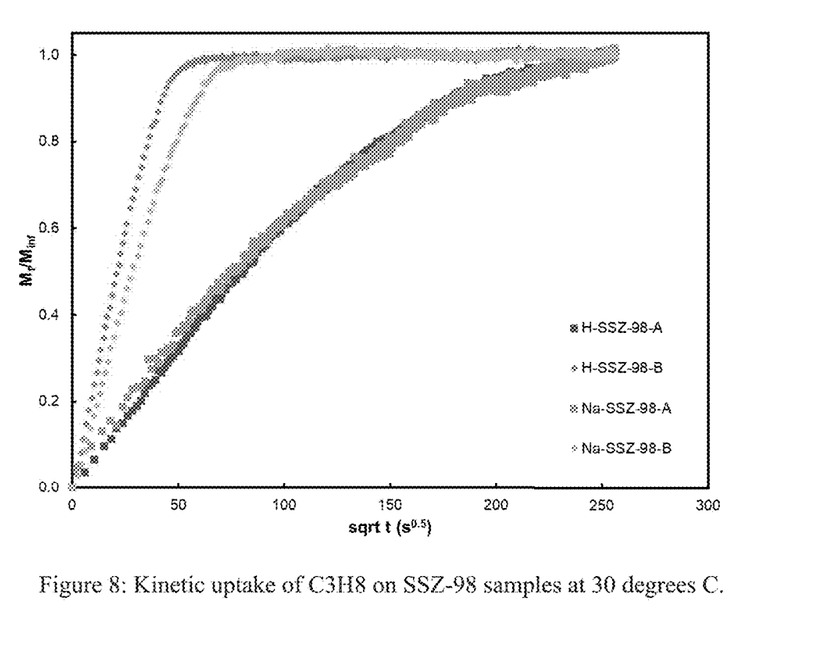
FIG. 8 is a plot of kinetic uptake of C3H8 on SSZ-98 samples at 30 degrees C.
Figure 9:
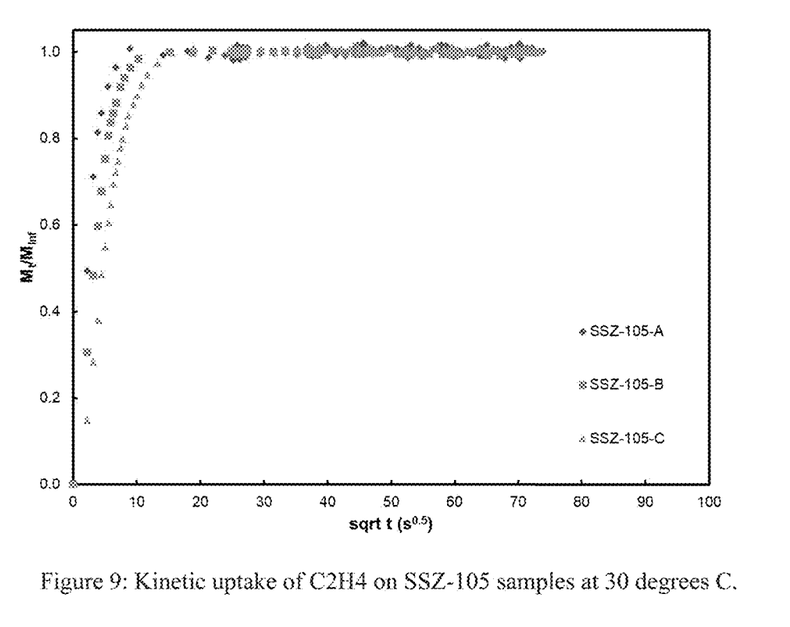
FIG. 9 is a plot of kinetic uptake of C2H4 on SSZ-105 samples at 30 degrees C.
Figure 10:
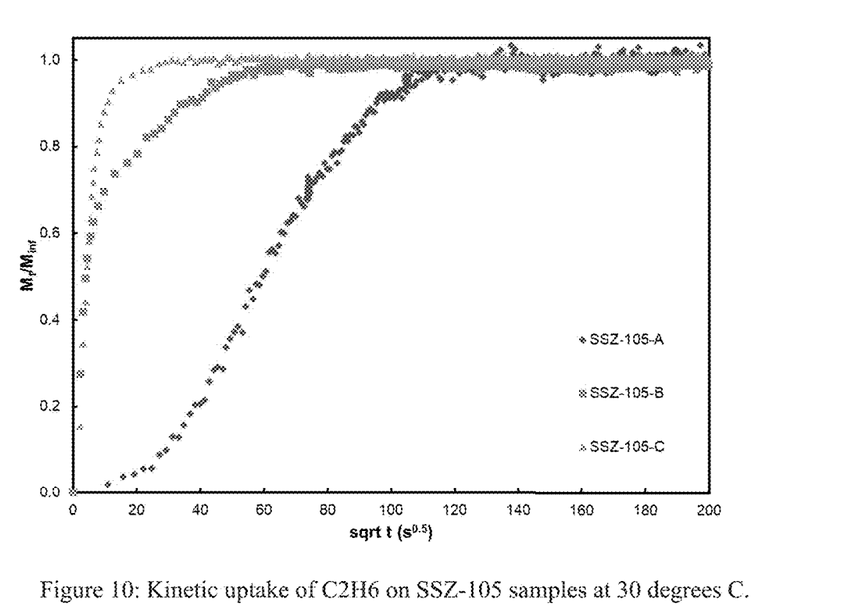
FIG. 10 is a plot of kinetic uptake of C2H6 on SSZ-105 samples at 30 degrees C.
Figure 11:
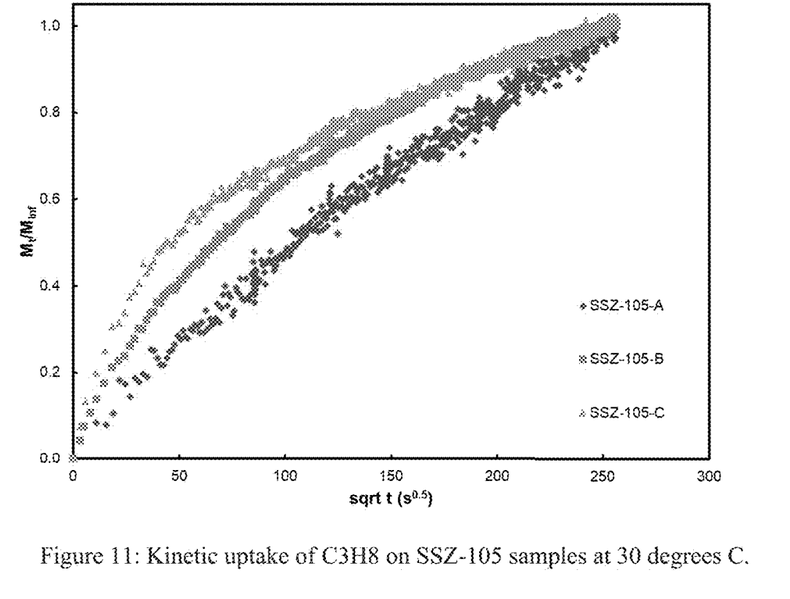
FIG. 11 is a plot of kinetic uptake of C3H8 on SSZ-105 samples at 30 degrees C.

Molecular sieving effects in the adsorption uptake of larger molecules found as impurities in ethylene streams such as ethane, propane and isobutane, relative to uptake of ethylene, plays an important role in recovery of ethylene from ethylene-stranded gases. Depending on the method of preparation for SSZ-98, including its calcination conditions and framework cation, such as hydrogen and sodium cations, SSZ-98 shows varying degrees of kinetic selectivity for C2H4/C2H6 diffusion separation and C2H4/C3H8 diffusion separation as compared to other small-pore zeolite materials. These gas pairs are important in recovery of ethylene from stranded ethylene-containing gases as molecules with three or more carbons can be difficult to remove if adsorbed onto the adsorbent material. Slow uptake allows the cycling of adsorbent to prevent complete uptake and maintain separation of the slower-adsorbing compounds during adsorption. FIGS. 6, 7 and 8 show kinetic uptake of C2H4, C2H6 and C3H8, respectively. As shown in FIG. 6, uptake of C2H4 is relatively fast among all SSZ-98 materials. In FIG. 7, there is appreciable difference in the uptake of C2H6 compared to C2H4 with SSZ-98-B samples that have either a hydrogen or a sodium framework cation, revealing that depending on preparation conditions the ethane diffusion may be slowed down in comparison to ethylene. In FIG. 8, an impurity found in ethylene gas streams, C3H8, shows extremely slow uptake among all SSZ-98 samples, such that the ERI framework phase enables selective rejection of propane adsorption on the adsorbent material and allows enhanced adsorption of ethylene.

Example 7: Kinetic Uptake of SSZ-105 Adsorbents

Depending on the method of preparation for SSZ-105, including the synthesis conditions that control the intergrowth of ERI and LEV frameworks and framework cation, such as hydrogen and sodium cations, SSZ-105 shows varying degrees of kinetic selectivity for C2H4/C2H6 diffusion separation and C2H4/C3H8 diffusion separation as compared to other small-pore zeolite materials. These gas pairs are important in recovery of ethylene from stranded ethylene-containing gases as molecules with three or more carbons can be difficult to remove if adsorbed onto the adsorbent material. Slow uptake allows the cycling of adsorbent to prevent complete uptake and maintain separation of the slower-adsorbing compounds during adsorption. FIGS. 5, 6 and 7 show kinetic uptake of C2H4, C2H6 and C3H8, respectively. As shown in FIG. 5, uptake of C2H4 is relatively fast among all SSZ-105 materials. In FIG. 6, there is appreciable difference in the uptake of C2H6 compared to C2H4 with SSZ-105-A samples, revealing that depending on selection of the intergrowth amount of ERI and LEV zeolite framework phases the ethane diffusion may be slowed down in comparison to ethylene. In FIG. 7, an impurity found in ethylene gas streams, C3H8, shows extremely slow uptake among all SSZ-105 samples. Comparison between SSZ-98 and SSZ-105 samples also shows that introduction of the LEV phase in the intergrowth of the zeolite can help further reduce the uptake diffusion rate for larger impurities such as propane in these gas streams.

The invention claimed is:

1. A method for removing impurities from a feed gas stream of ethylene-containing stranded gas including impurities and ethylene, comprising:
    (a) alternating an input of the feed gas stream between at least two beds of a one or more adsorbent particles made from a homogeneous mixture, wherein the one or more adsorbent particles comprise a zeolite SSZ-98 or a zeolite SSZ-105;
    (b) wherein the feed gas stream contacts one of the at least two beds at a given time by an adsorption step and a product gas stream is simultaneously vented from another of the at least two beds by a desorption step;
    (c) wherein a contacting in the one of the at least two beds occurs at a feed pressure of from about 345 kPa to about 3450 kPa for a sufficient time to preferentially adsorb the ethylene from the feed gas stream and thereby producing a product gas stream during the desorption step containing no greater than about 2 mol % impurities, at least about 98 mol % of the ethylene recovered from the feed gas stream; and
    (d) wherein the feed gas stream is input at a feed end of each of the at least two beds, the product gas stream is removed from the feed end of each of the at least two beds during the desorption step, and an impurity-enriched gas stream is produced from the tail gas end of the at least two beds.

2. The method of claim 1 wherein the impurities are nitrogen, hydrogen, propane, isobutane and ethane.

3. The method of claim 1, wherein the zeolite SSZ-98 or the zeolite SSZ-105 has a Si:Al mole ratio of from 5 to 100.

4. The method of claim 1, wherein the zeolite SSZ-98 or the SSZ-105 has a cation as a framework ion and the cation is selected from the group consisting of a sodium, a calcium, a potassium, a lithium, a magnesium, a barium, a hydrogen, a copper, a platinum, a paladium and combinations thereof.

5. The method of claim 4, wherein the cation is the sodium.

6. The method of claim 4, wherein the cation is the hydrogen.

7. The method of claim 4, wherein the cation is the copper.

8. The method of claim 1, wherein the method utilizes two beds of the one or more adsorbent particles, and further comprising:
    (a) following the adsorption step in one of the two beds and a simultaneous desorption step in the other of the two beds, equalizing a pressure of the one of the two beds and the other of the two beds through the feed end of each of the one of the two beds and the other of the two beds at an end of the adsorption and the simultaneous desorption step; and
    (b) re-pressurizing the other of the two beds having just completed the simultaneous desorption step by sending a slipstream of the product gas stream through the feed end of the other of the two beds having just completed the simultaneous desorption step.

9. The method of claim 1, wherein the method utilizes two beds of the one or more adsorbent particles, and further comprising:
    (a) following the adsorption step in one of the two beds and a simultaneous desorption step in the other of the two beds, equalizing a pressure of the one of the two beds and the other of the two beds through the tail gas end of each of the one of the two beds and the other of the two beds at an end of the adsorption and the simultaneous desorption step; and
    (b) re-pressurizing the other of the two beds having just completed the simultaneous desorption step by sending a slipstream of the product gas stream through the tail gas end of the other of the two beds having just completed the simultaneous desorption step.

* * * * *